United States Patent
Stenger-Smith et al.

(10) Patent No.: US 9,862,694 B1
(45) Date of Patent: Jan. 9, 2018

(54) METHOD FOR THE SYNTHESIS AND PURIFICATION OF ETHERS

(71) Applicant: The United States of America, as represented by the Secretary of the Navy, Washington, DC (US)

(72) Inventors: John D Stenger-Smith, Ridgecrest, CA (US); Paul A. Goodman, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 117 days.

(21) Appl. No.: 14/736,594

(22) Filed: Jun. 11, 2015

(51) Int. Cl.
*C07D 307/12* (2006.01)

(52) U.S. Cl.
CPC ................... *C07D 307/12* (2013.01)

(58) Field of Classification Search
CPC .................................................. C07D 307/12
See application file for complete search history.

(56) References Cited

U.S. PATENT DOCUMENTS 4,305,878 A    12/1981 Chu et al.

OTHER PUBLICATIONS

Kirner, W. "Alpha-Tetrahydrofurfuryl Chloride and Alpha-Tetrahydrofurfuryl Ethers." J. Am. Chen. Soc. (Aug. 1930), vol. 52, pp. 3251-3256.*

Georgia State University. "Work Functions for Photoelectric Effect." © Feb. 25, 2013. Available from: < http://web.archive.org/web/20130225080920/http://hyperphysics.phy-astr.gsu.edu/hbase/tables/photoelec.html >.*
Chem4Kids. "Metal Basics." (c) Mar. 12, 2010. Available from: < http://web.archive.org/web/20100312044514/http://www.chem4kids.com/files/elem_metal.html >.*
University of California at Berkeley. "Chemical Class Standard Operating Procedures: Strong Reducing Agents (SRA)." (c) Jun. 3, 2013. Available from: < http://www.cchem.berkeley.edu/rsgrp/SOPs2013/StrongReducingAgents_Sarpong.pdf >.*
PerkinElmer. "ChemBioDraw." © 2014.*
University of Texas at Austin. "Alcohol." © 2016. Available from: <http://colapret.cm.utexas.edu/courses/Nomenclature_files/alcohols.htm >.*
W. R. Kirner, Alpha-Tetrahydrofurfuryl Chloride and Alpha-Tetrahydrofurfuryl Ethers, Journal of the American Chemical Society, 1930, 3251, 52.
Cao, et al., Solid acid-catalyzed conversion of furfuryl alcohol to alkyl tetrahydrofurfuryl ether,Catalysis Communications, 2015, pp. 76-79,vol. 58.
L. M. Prutkov, I. K. Sanin, I. V. Kamenskii, Bis(tetrahydrofurfuryl) ether, Khim. Geterotsikl. Soedin., 1966, 632.

* cited by examiner

*Primary Examiner* — Noble E Jarrell
*Assistant Examiner* — John S Kenyon
(74) *Attorney, Agent, or Firm* — Stuart H. Nissim

(57) ABSTRACT

Methods of synthesizing and purifying ethers are described. The synthesis and purification are achieved using an etherification technique followed by one or two fractional distillations. The etherification utilizes an element having low work function properties. Examples of low work function elements include, but are not limited to, metals or their hydrides, such as sodium, lithium or potassium or some combination thereof. This technique yields ethers of greater than 90% purity.

8 Claims, No Drawings

METHOD FOR THE SYNTHESIS AND PURIFICATION OF ETHERS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to the synthesis and purification of ethers.

BACKGROUND OF THE INVENTION

Ethers are an important raw material, solvent, and intermediate used in organic synthesis, as oxygenators for fuels, as diesel fuel additives, in pharmaceuticals, in agrochemicals, in refrigeration applications, as flavoring agents, and in many other applications.

A number of scientific publications and patents have studied, or proposed, the use of alkyl tetrahydrofurfuryl ethers, for example, for a diverse array of applications. In 1930, Kirner synthesized a small library of alkyl tetrahydrofurfuryl ethers, and analyzed their use as an anesthetic and their toxicity in mice and guinea pigs. W. R. Kirner, Alpha-Tetrahydrofurfuryl Chloride and Alpha-Tetrahydrofurfuryl Ethers, *Journal of the American Chemical Society*, 1930, 52, 3251. Some published works show the utility of these compounds as structural modifiers in rubbers. Modification of rubber with various alkyl tetrahydrofurfuryl ethers increases the static friction coefficient of the product. Additionally, these compounds have been proposed as components of heat pumps, paint strippers, and as fuel additives.

There is a large market for these compounds, and there are proposed methods for their synthesis. For example, current syntheses of ethyl tetrahydrofurfuryl ether (ETFE) are described in U.S. Pat. No. 4,305,878 to Chu, et al. The method disclosed in the Chu et al. patent describes the purification of ETFE via multiple extractions using multiple calcium chloride and other aqueous salts, followed by fractional distillation. Chu specifically states the difficulty in separating ETFE from tetrahydrofurfuryl alcohol (THFA) and alcohol using distillation and that multiple aqueous extractions were required to remove THFA to below acceptable levels. This requirement for multiple extractions and distillations is both inefficient and undesirable.

Cao, et al., "Solid acid-catalyzed conversion of furfuryl alcohol to alkyl tetrahydrofurfuryl ether", 2015, Catalysis Communications, Volume 58, Pages 76-79) disclose a cumbersome process which uses at least two (2) separate catalytic steps with low yields (ETFE—40.6% [at 55° C.]) and low purity.

One tetrahydrofurfuryl ether that has been cited as difficult to obtain is bis(tetrahydrofurfuryl) ether (BTHFE). The one previous report of its synthesis lacked an in-depth characterization of the compound, leaving some doubt as to the true identity of the reported product. L. M. Prutkov, I. K. Sanin, I. V. Kamenskii, *Bis(tetrahydrofurfuryl) ether*, Khim. Geterotsikl. Soedin, 632 (1966).

The current invention provides novel synthesis and purification techniques in which no extractions are necessary, and in which at least 90% purity, and greater than 98% purity ether has been obtained in one or two steps using fractional distillation in the presence of an excess of a reactive element. This method is particularly useful for the synthesis and purification of tetrahydrofurfuryl ethers, such as alkyl tetrahydrofurfuryl and bis(tetrahydrofurfuryl) ethers.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments.

DETAILED DESCRIPTION OF THE INVENTION

The present invention relates to the synthesis and purification of ethers, preferred ethers include alkyl tetrahydrofurfuryl ethers (TFE), for example, ethyl tetrahydrofurfuryl ether (ETFE) having the formula:

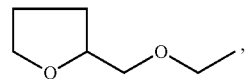

and
bis(tetrahydrofurfuryl) ethers (BTHFE) having the formula:

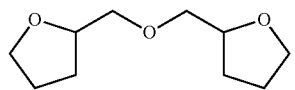 [SMILES: C1COC(COCC2CCCO2)C1]

In the method of the present invention tetrahydrofurfuryl alcohol (THFA) is mixed with up to about a molar equivalent amount of a source of a low work function element. After the reaction of THFA with the low work function element is complete, a halide is added drop wise and the reaction mixture is heated overnight under inert gas. The resulting mixture is fractionally distilled with all distillate collected in a flask. This first distillate is found to have a roughly 50/50 mixture of THFA and a tetrahydrofurfuryl ether. The distillate is then reacted (with heating) with sufficient low work function element (which can be the same or different than the low work function element previously used), until all of the THFA is reacted—this is evidenced by the presence of unreacted low work function element. This distillate containing the unreacted low work function element is then fractionally distilled; the distillate is shown to contain purified tetrahydrofurfuryl ether.

An alternative embodiment of the method involves the reaction of THFA with approximately ½ equivalent of low work function element. After the reaction of THFA with the low work function element is complete, ½ an equivalent of a halide is added and the reaction mixture is heated overnight under nitrogen. The remaining ½ of equivalent of low work function element and ½ equivalent of halide are then added and the reaction is heated overnight under nitrogen. When this reaction is complete, small amounts of low work function element are added until unreacted low work function element is detected. This mixture is then fractionally distilled and the collected distillate is shown to contain purified tetrahydrofurfuryl ether.

The work function of an element corresponds to the minimum amount of energy needed to remove an electron from the element (i.e., an electron from the highest filled level in the Fermi distribution of a solid so that it is stationary at a point in a field-free zone just outside the solid, at absolute zero). In metals, work function and ionization energy are the same.

Designated as φ, and presented in units of electron volts (eV), preferred low work function elements for the present invention have a φ value of less than about 3.0 eV. Such elements include, but are not limited to: barium (φ=2.52–2.7 eV), calcium (φ=2.87 eV), cerium (φ=2.9 eV), cesium (φ=2.14 eV), europium (φ=2.5 eV), gadolinium (φ=2.90 eV), potassium (φ=2.29 eV), lithium (φ=2.9 eV), sodium (φ=2.36 eV), rubidium (φ=2.261 eV), samarium (φ=2.7 eV), strontium (φ=~2.59 eV), and ytterbium (φ=2.6 eV).

Preferred sources of low work function elements are metals and metal hydrides. A preferred low work function element is a reducing agent. Examples of preferred low work function elements include, but are not limited to, elemental magnesium metal, lithium hydride, potassium hydride, rubidium hydride, cesium hydride, magnesium hydride, and calcium hydride. Sodium is a preferred low work function element due to its low cost, ready availability, ease of use, and high reactivity. The method of the invention can utilize one or more low work function elements or combinations thereof.

Halides used in the method of the present invention can include fluorides, chlorides, bromides, iodides, or astatides, preferably a bromide or chloride, more preferably a bromide. Halides have the formula XR, where R can be a substituted or unsubstituted alkyl, alkenyl, or alkynyl of 1 to 20 carbon atoms, a substituted or unsubstituted heterocycle, or a substituted or unsubstituted phenyl, preferably an alkyl of from 1 to 10 carbon atoms and X is F, Cl, Br, I, or At.

In one preferred embodiment, ETFE is formed by the reaction of tetrahydrofurfuryl alcohol (THFA), ethyl chloride or ethyl bromide, and sodium hydride or sodium. In the method of the present invention tetrahydrofurfuryl alcohol (THFA) is mixed with about a less than molar equivalent amount of sodium hydride or sodium. After the reaction of THFA with the sodium hydride or sodium is complete, ethyl chloride or ethyl bromide is added drop wise and the reaction mixture is heated overnight under inert gas. The resulting mixture is fractionally distilled with all distillate boiling at around 158-162 degrees C. collected in a flask. This first distillate is found to have a roughly 50/50 mixture of THFA and ethyl tetrahydrofurfuryl ether. The distillate is then reacted (with heating) with sufficient sodium hydride or sodium (which can be the same or different than previously used), until all the THFA is reacted—this is evidenced by the presence of unreacted low work function element. This distillate containing the unreacted sodium hydride or sodium is then fractionally distilled, collecting the material boiling between 154 and 158 degrees Celsius at 0.91 atmosphere pressure, which is shown to contain purified ethyl tetrahydrofurfuryl ether.

EXAMPLES

Example 1

220 mL (230.645 g, 2.26 moles) of tetrahydrofurfuryl alcohol was put in a 500 mL round bottom flask equipped with a stir bar and under nitrogen gas at room temperature. 8.43 grams (0.37 moles) of sodium metal was added and the reaction was allowed to proceed to completion forming the sodium salt of tetrahydrofurfuryl oxide ($C_5H_9O_2Na$). The contents were heated during the reaction to about 60 degrees C. to insure the mixture remained liquid. A total of 27.25 mL (39.8 g, 0.37 moles) of ethyl bromide was added dropwise over the course of several hours. The reaction mixture was then heated to reflux overnight; boiling occurred at about 75 degrees C. The mixture was then fractionally distilled and all the material (about 40 grams) that boiled between 145 and 160 degrees Celsius was collected. The distillate was then put in a 100 mL round bottom flask and sufficient sodium to react with any impurities was added, then a small excess of sodium was added. The presence of metallic sodium was used as an indication that an excess of sodium as added. This material was fractionally distilled and the distillate that boiled between 154 and 157 degrees Celsius at 0.91 atm pressure was collected. The material, 16.4 grams (35% yield based upon limiting reactant sodium) was analyzed by Gas Chromatography/Mass Spectrometry and was found to be 99.8% pure (commercially purchased ETFE was found to be 99.6% pure)

Example 2

100 mL (104 g, 1.01 moles) of tetrahydrofurfuryl alcohol was put in a 500 mL round bottom flask equipped with a stir bar and under nitrogen gas. 9.8 grams (0.43 moles) of sodium metal was added and the reaction was allowed to proceed to completion. The contents were heated during the reaction between 50 and 80 degrees C. to insure the mixture remained liquid. 32 mL (32.0 g, 0.29 moles) of ethyl bromide was added dropwise over the course of several hours. The reaction mixture was then heated to reflux overnight. The mixture was then fractionally distilled and all the material (about 54.5 grams) that boiled between 145 and 160 degrees Celsius was collected. The distillate was then put in a 200 mL round bottom flask and sufficient (7.5 grams, 0.33 moles) sodium to react with any impurities was added. The presence of metallic sodium was used as an indication that an excess of sodium as added. This material was fractionally distilled and the fraction that boiled between 154 and 157 degrees Celsius at 0.91 atm pressure was collected. The material, 30 grams (52% based upon limiting reactant sodium and 30% based upon THFA) was analyzed by Gas Chromatography/Mass Spectrometry and was found to be 99.7% pure.

The residue of the second distillation was then put into the residue of the first fractional distillation and the excess sodium was allowed to completely react. 24.5 mL (35.8 g, 0.33 moles) of ethyl bromide was then added dropwise over several hours, and then the reaction was heated to reflux for 12 hours. The mixture as cooled, an additional 2 grams of sodium was added to provide excess sodium and this mixture was fractionally distilled and the fraction that boiled between 154 and 157 degrees Celsius at 0.91 atm pressure was collected (an additional 26 grams) was collected. The product was analyzed by Gas Chromatography/Mass Spectrometry and found to be 99.7% pure. The overall yield based upon THFA was 56%.

Example 3

12.4 mL (13.0 g, 0.128 moles) of tetrahydrofurfuryl alcohol was put in a 50 mL round bottom flask equipped with a stir bar and under nitrogen gas. 1.4 grams (0.06 moles) of sodium metal was added, heated to between 40 and 70 degrees C., and the reaction was allowed to proceed to completion. Ethyl bromide (5 mL, 7.3 g, 0.07 moles) was added drop-wise over the course of several hours. The reaction was refluxed for several hours. The reaction was cooled then an additional 1.4 grams (0.061 moles) of sodium metal was added and the reaction was allowed to proceed to completion. An additional 5 mL (7.3 g, 0.031 moles) of ethyl bromide was added drop-wise over the course of several hours. The mixture was cooled, and sufficient sodium was added (with careful heating under nitrogen) until unreacted sodium was detected. The mixture was then fractionally distilled and the fraction that boiled between 154 and 157 degrees Celsius at 0.91 atm pressure was collected (9.6 grams of product). Chromatography/Mass Spectrometry and was found to be 99.6% pure (the commercially purchased ETFE was found to be 99.6% pure). The overall yield based upon THFA was 57%.

Example 4

20.0 mL (20.4 g 0.206 moles) of tetrahydrofurfuryl alcohol was put in a 50 mL round bottom flask equipped with a stir bar and under nitrogen gas. 4.8 grams (0.21 moles) of sodium metal was added and the reaction was allowed to proceed to completion at a temperature between 40° and 70° C. 22.5 mL (32.8 g, 0.30 moles) of ethyl bromide was added drop-wise over the course of several hours. The reaction was refluxed for 3 days. The reaction was cooled then filtered. An additional 5 mL of ethyl bromide was added drop-wise over the course of several hours. The mixture was cooled, and sufficient sodium was added (with careful heating under nitrogen) until unreacted sodium was detected. The mixture was then fractionally distilled under low pressure and the fraction that boiled between 154 and 157 degrees Celsius at 0.13 atm pressure was collected 9.6 grams of product was collected. Chromatography/Mass Spectrometry and was found to be 99.6% pure (the commercially purchased ETFE was found to be 99.6% pure). The overall yield based upon THFA was 57%.

Example 5

Synthesis of 2-Methanesulfonylmethyltetrahydrofuran

A 3-neck round bottom flask was filled with 200 mL pyridine and 88 mL (91.8 g, 0.90 moles) of THFA. An addition funnel was added, the mixture was placed in an ice/water bath, and purged with nitrogen for 1 hour. Methanesulfonyl chloride (73 mL, 108.4 g, 0.94 moles) was added drop wise to the continuously chilled mixture over 12 hours. The mixture was then allowed to warm to room temperature over the next 48 hours, at which time it was combined with 500 mL of 1.2 M HCl, and extracted three times with 125 mL portions of dichloromethane. The organic phases were combined and then extracted once with 125 mL of 1.2 M HCl, followed by 125 mL of saturated NaCl. Finally, the dichloromethane solution was dried with MgSO4, and the solvent was removed under reduced pressure. The crude product was a light yellow liquid, and the yield of crude material was 144 grams (89%). Portions of the crude material were vacuum distilled at 0.34 mmHg to obtain pure product, which was a clear, colorless liquid. This material was characterized by 1H and 13C NMR, 2-D NMR, GC/Mass Spectrometry, Infrared Spectroscopy, and elemental analysis. 1H NMR: 1.60 m (1H); 1.8 m (2H); 1.9 m (1H); 3.03 s, (3H); 3.76 m (2H); 4.0 m (2H); 4.14 m (1H). 13C NMR: 76.29, 71.65, 68.60, 37.55, 27.60, 25.75. Elemental Analysis: Calculated: 39.93% C; 6.71% H; 17.79% S. Found: 40.1% C; 6.7% H; 18:01% S. GC/MS indicates 98.6% purity.

Synthesis of bis(tetrahydrofurfuryl) ether

A 2-neck round bottom flask was filled with 25 mL of THF and 8.36 g (0.67 moles) of the sodium salt of THFA, which was prepared by adding sodium metal to excess THFA, and collecting the resulting solid. The mixture was placed under a nitrogen flow, heated to approximately 70 degrees Celsius using an oil bath, and 12.1 g (0.74 moles) of 2-methanesulfonylmethyltetrahydrofuran was added drop wise over the course of several hours. Then, the temperature of the oil was raised to approximately 170 degrees Celsius, and the THF was allowed to evaporate while the progress of the reaction was monitored by removing small aliquots from the mixture and recording the NMR spectrum. The mixture was allowed to cool to room temperature when the NMR spectrum indicated that the reaction was approximately 90% complete (after roughly 48 hours). Diethyl ether (100 mL) was added to the room temperature mixture, which was then filtered, and the ether was removed by rotary evaporation. Yield of crude material, which was a brown colored liquid, was 8.25 g. The crude material was purified by vacuum distillation, and temperature of the distillate was 48 degrees Celsius at 0.43 mmHg. This material was found to be approximately 99% pure by GC-MS. Elemental Analysis: Calculated: 64.48% C; 9.74% H; 25.75% O. Found: 63.71% C; 9.89% H; 26.4% O.

It is to be understood that the foregoing examples are exemplary and explanatory only and are not to be viewed as being restrictive of the invention, as claimed. The present invention is not limited to the production and purification of ETFE. The present processes and methods can be used to make and purify any type of ether by one skilled in the art and, as such, does not invalidate the spirit and method of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed:

1. A method of synthesizing and purifying an ether, comprising:
   reacting a mixture of tetrahydrofurfuryl alcohol and up to about one equivalent of at least one low work function element;
   reacting said mixture with a halide;
   fractionally distilling said reacted mixture to yield a first distillate;
   reacting said first distillate with an excess amount of at least one low work function element; and,
   fractionally distilling said reacted first distillate to obtain the purified ether wherein said at least one low work function element is an elemental metal or a metal hydride which has a $\varphi$ of less than about 3.0 eV.

2. The method according to claim 1 wherein said low work function element is selected from the group consisting of elemental sodium metal, elemental lithium metal, elemental potassium metal, elemental rubidium metal, elemental cesium metal, elemental magnesium metal, elemental calcium metal, sodium hydride, lithium hydride, potassium hydride, rubidium hydride, cesium hydride, magnesium hydride, calcium hydride, and combinations thereof.

3. The method according to claim 1 wherein said ether is of purity greater than about 90%.

4. The method according to claim 1 wherein said halide has the formula RX, where R is an alkyl, alkenyl, alkynyl, substituted heterocycle, unsubstituted heterocycle, substituted phenyl, or unsubstituted phenyl, having 1 to 20 carbon atoms and where X is a halogen.

5. The method according to claim 1, wherein said ether is an alkyl ether of tetrahydrofurfuryl alcohol, said alkyl comprising 1 to 22 carbon atoms.

6. The method according to claim 1 wherein said ether is di-tetrahydrofurfuryl ether.

7. The method according to claim 1, wherein said low work function element is elemental sodium metal or sodium hydride.

8. The method according to claim 1, wherein said low work function metal is a reducing agent.

* * * * *